United States Patent
Moriyama et al.

(10) Patent No.: US 11,980,412 B2
(45) Date of Patent: May 14, 2024

(54) ELONGATED MEDICAL SHEATH

(71) Applicant: Boston Scientific Medical Device Limited, Galway (IE)

(72) Inventors: Eduardo Moriyama, Richmond (CA); Lauren Koon, Mississauga (CA)

(73) Assignee: Boston Scientific Medical Device Limited, Galway (IE)

( * ) Notice: Subject to any disclaimer, the term of this patent is extended or adjusted under 35 U.S.C. 154(b) by 261 days.

(21) Appl. No.: 17/404,444

(22) Filed: Aug. 17, 2021

(65) Prior Publication Data

US 2022/0079654 A1 Mar. 17, 2022

Related U.S. Application Data

(60) Provisional application No. 63/078,545, filed on Sep. 15, 2020.

(51) Int. Cl.
*A61B 18/14* (2006.01)
*A61B 18/00* (2006.01)

(52) U.S. Cl.
CPC .... *A61B 18/14* (2013.01); *A61B 2018/00214* (2013.01); *A61B 2018/00601* (2013.01); *A61B 2018/141* (2013.01)

(58) Field of Classification Search
CPC ................ A61B 18/14; A61B 18/1492; A61B 2018/00214; A61B 2018/00267; A61B 2018/00357; A61B 2018/00601; A61B 2018/00839; A61B 2018/141
See application file for complete search history.

(56) References Cited

U.S. PATENT DOCUMENTS

| | | | |
|---|---|---|---|
| 175,254 | A | 3/1876 | Oberly |
| 827,626 | A | 7/1906 | Gillet |
| 848,711 | A | 4/1907 | Weaver |
| 1,072,954 | A | 9/1913 | Junn |
| 1,279,654 | A | 9/1918 | Charlesworth |
| 1,918,094 | A | 7/1933 | Geekas |
| 1,996,986 | A | 4/1935 | Weinberg |
| 2,021,989 | A | 11/1935 | De Master |
| 2,146,636 | A | 2/1939 | Lipchow |
| 3,429,574 | A | 2/1969 | Williams |
| 3,448,739 | A | 6/1969 | Stark et al. |
| 3,575,415 | A | 4/1971 | Fulp et al. |
| 3,595,239 | A | 7/1971 | Petersen |
| 4,129,129 | A | 12/1978 | Amrine |
| 4,244,362 | A | 1/1981 | Anderson |
| 4,401,124 | A | 8/1983 | Guess et al. |
| 4,639,252 | A | 1/1987 | Kelly et al. |
| 4,641,649 | A | 2/1987 | Walinsky et al. |
| 4,669,467 | A | 6/1987 | Willett et al. |
| 4,682,596 | A | 7/1987 | Bales et al. |
| 4,790,311 | A | 12/1988 | Ruiz |

(Continued)

*Primary Examiner* — Michael F Peffley

(74) *Attorney, Agent, or Firm* — Nelson Mullins Riley & Scarborough LLP

(57) ABSTRACT

An elongated medical sheath is configured to be movable and positionable proximate to a biological feature of a patient. An expandable-and-collapsible support structure is configured to be selectively movable, at least in part, between an interior of the elongated medical sheath and an exterior of the elongated medical sheath. An energy-emitting assembly is supported by the expandable-and-collapsible support structure.

20 Claims, 3 Drawing Sheets

(56) References Cited

U.S. PATENT DOCUMENTS

| | | |
|---|---|---|
| 4,790,809 A | 12/1988 | Kuntz |
| 4,793,350 A | 12/1988 | Mar et al. |
| 4,807,620 A | 2/1989 | Strul et al. |
| 4,832,048 A | 5/1989 | Cohen |
| 4,840,622 A | 6/1989 | Hardy |
| 4,863,441 A | 9/1989 | Lindsay et al. |
| 4,884,567 A | 12/1989 | Elliott et al. |
| 4,892,104 A | 1/1990 | Ito et al. |
| 4,896,671 A | 1/1990 | Cunningham et al. |
| 4,928,693 A | 5/1990 | Goodin et al. |
| 4,936,281 A | 6/1990 | Stasz |
| 4,960,410 A | 10/1990 | Pinchuk |
| 4,977,897 A | 12/1990 | Hurwitz |
| 4,998,933 A | 3/1991 | Eggers et al. |
| 5,006,119 A | 4/1991 | Acker et al. |
| 5,019,076 A | 5/1991 | Yamanashi et al. |
| 5,047,026 A | 9/1991 | Rydell |
| 5,081,997 A | 1/1992 | Bosley et al. |
| 5,098,431 A | 3/1992 | Rydell |
| 5,112,048 A | 5/1992 | Kienle |
| 5,154,724 A | 10/1992 | Andrews |
| 5,201,756 A | 4/1993 | Horzewski et al. |
| 5,209,741 A | 5/1993 | Spaeth |
| 5,211,183 A | 5/1993 | Wilson |
| 5,221,256 A | 6/1993 | Mahurkar |
| 5,230,349 A | 7/1993 | Langberg |
| 5,281,216 A | 1/1994 | Klicek |
| 5,300,068 A | 4/1994 | Rosar et al. |
| 5,300,069 A | 4/1994 | Hunsberger et al. |
| 5,314,418 A | 5/1994 | Takano et al. |
| 5,318,525 A | 6/1994 | West et al. |
| 5,327,905 A | 7/1994 | Avitall |
| 5,364,393 A | 11/1994 | Auth et al. |
| 5,372,596 A | 12/1994 | Klicek et al. |
| 5,380,304 A | 1/1995 | Parker |
| 5,397,304 A | 3/1995 | Truckai |
| 5,403,338 A | 4/1995 | Milo |
| 5,423,809 A | 6/1995 | Klicek |
| 5,425,382 A | 6/1995 | Golden et al. |
| 5,490,859 A | 2/1996 | Mische et al. |
| 5,497,774 A | 3/1996 | Swartz et al. |
| 5,507,751 A | 4/1996 | Goode et al. |
| 5,509,411 A | 4/1996 | Littmann et al. |
| 5,540,681 A | 7/1996 | Strul et al. |
| 5,545,200 A | 8/1996 | West et al. |
| 5,555,618 A | 9/1996 | Winkler |
| 5,571,088 A | 11/1996 | Lennox et al. |
| 5,575,766 A | 11/1996 | Swartz et al. |
| 5,575,772 A | 11/1996 | Lennox |
| 5,599,347 A | 2/1997 | Hart et al. |
| 5,605,162 A | 2/1997 | Mirzaee et al. |
| 5,617,878 A | 4/1997 | Taheri |
| 5,622,169 A | 4/1997 | Golden et al. |
| 5,624,430 A | 4/1997 | Eton et al. |
| 5,667,488 A | 9/1997 | Lundquist et al. |
| 5,673,695 A | 10/1997 | McGee et al. |
| 5,674,208 A | 10/1997 | Berg et al. |
| 5,680,860 A * | 10/1997 | Imran ............... A61B 18/1492 606/41 |
| 5,683,366 A | 11/1997 | Eggers et al. |
| 5,720,744 A | 2/1998 | Eggleston et al. |
| 5,741,249 A | 4/1998 | Moss et al. |
| 5,766,135 A | 6/1998 | Terwilliger |
| 5,779,688 A | 7/1998 | Imran et al. |
| 5,810,764 A | 9/1998 | Eggers et al. |
| 5,814,028 A | 9/1998 | Swartz et al. |
| 5,830,214 A | 11/1998 | Flom et al. |
| 5,836,875 A | 11/1998 | Webster, Jr. |
| 5,849,011 A | 12/1998 | Jones et al. |
| 5,851,210 A | 12/1998 | Torossian |
| 5,885,227 A | 3/1999 | Finlayson |
| 5,888,201 A | 3/1999 | Stinson et al. |
| 5,893,848 A | 4/1999 | Negus et al. |
| 5,893,885 A | 4/1999 | Webster, Jr. |
| 5,904,679 A | 5/1999 | Clayman |
| 5,916,210 A | 6/1999 | Winston |
| 5,916,235 A | 6/1999 | Guglielmi |
| 5,921,957 A | 7/1999 | Killion et al. |
| 5,931,818 A | 8/1999 | Werp et al. |
| 5,944,023 A | 8/1999 | Johnson et al. |
| 5,951,482 A | 9/1999 | Winston et al. |
| 5,957,842 A | 9/1999 | Littmann et al. |
| 5,964,757 A | 10/1999 | Ponzi |
| 5,967,976 A | 10/1999 | Larsen et al. |
| 5,989,276 A | 11/1999 | Houser et al. |
| 6,007,555 A | 12/1999 | Devine |
| 6,009,877 A | 1/2000 | Edwards |
| 6,013,072 A | 1/2000 | Winston et al. |
| 6,017,340 A | 1/2000 | Cassidy et al. |
| 6,018,676 A | 1/2000 | Davis et al. |
| 6,030,380 A | 2/2000 | Auth et al. |
| 6,032,674 A | 3/2000 | Eggers et al. |
| 6,048,349 A | 4/2000 | Winston et al. |
| 6,053,870 A | 4/2000 | Fulton, III |
| 6,053,904 A | 4/2000 | Scribner et al. |
| 6,056,747 A | 5/2000 | Saadat et al. |
| 6,063,093 A | 5/2000 | Winston et al. |
| 6,093,185 A | 7/2000 | Ellis et al. |
| 6,106,515 A | 8/2000 | Winston et al. |
| 6,106,520 A | 8/2000 | Laufer et al. |
| 6,117,131 A | 9/2000 | Taylor |
| 6,142,992 A | 11/2000 | Cheng et al. |
| 6,146,380 A | 11/2000 | Racz et al. |
| 6,155,264 A | 12/2000 | Ressemann et al. |
| 6,156,031 A | 12/2000 | Aita et al. |
| 6,171,305 B1 | 1/2001 | Sherman |
| 6,179,824 B1 | 1/2001 | Eggers et al. |
| 6,193,676 B1 | 2/2001 | Winston et al. |
| 6,193,715 B1 | 2/2001 | Wrublewski et al. |
| 6,210,408 B1 | 4/2001 | Chandrasekaran et al. |
| 6,217,575 B1 | 4/2001 | Devore et al. |
| 6,221,061 B1 | 4/2001 | Engelson et al. |
| 6,228,076 B1 | 5/2001 | Winston et al. |
| 6,245,054 B1 | 6/2001 | Fuimaono et al. |
| 6,267,758 B1 | 7/2001 | Daw et al. |
| 6,283,983 B1 | 9/2001 | Makower et al. |
| 6,292,678 B1 | 9/2001 | Hall et al. |
| 6,293,945 B1 | 9/2001 | Parins et al. |
| 6,296,615 B1 | 10/2001 | Brockway et al. |
| 6,296,636 B1 | 10/2001 | Cheng et al. |
| 6,302,898 B1 | 10/2001 | Edwards et al. |
| 6,304,769 B1 | 10/2001 | Arenson et al. |
| 6,315,777 B1 | 11/2001 | Comben |
| 6,328,699 B1 | 12/2001 | Eigler et al. |
| 6,360,128 B2 | 3/2002 | Kordis et al. |
| 6,364,877 B1 | 4/2002 | Goble et al. |
| 6,385,472 B1 | 5/2002 | Hall et al. |
| 6,394,976 B1 | 5/2002 | Winston et al. |
| 6,395,002 B1 | 5/2002 | Ellman et al. |
| 6,419,674 B1 | 7/2002 | Bowser et al. |
| 6,428,551 B1 | 8/2002 | Hall et al. |
| 6,450,989 B2 | 9/2002 | Dubrul et al. |
| 6,475,214 B1 | 11/2002 | Moaddeb |
| 6,485,485 B1 | 11/2002 | Winston et al. |
| 6,508,754 B1 | 1/2003 | Liprie et al. |
| 6,524,303 B1 | 2/2003 | Garibaldi |
| 6,530,923 B1 | 3/2003 | Dubrul et al. |
| 6,554,827 B2 | 4/2003 | Chandrasekaran et al. |
| 6,562,031 B2 | 5/2003 | Chandrasekaran et al. |
| 6,562,049 B1 | 5/2003 | Norlander et al. |
| 6,565,562 B1 | 5/2003 | Shah et al. |
| 6,607,529 B1 | 8/2003 | Jones et al. |
| 6,632,222 B1 | 10/2003 | Edwards et al. |
| 6,639,999 B1 | 10/2003 | Cookingham et al. |
| 6,650,923 B1 | 11/2003 | Lesh et al. |
| 6,651,672 B2 | 11/2003 | Roth |
| 6,662,034 B2 | 12/2003 | Segner et al. |
| 6,663,621 B1 | 12/2003 | Winston et al. |
| 6,702,811 B2 | 3/2004 | Stewart et al. |
| 6,709,444 B1 | 3/2004 | Makower |
| 6,723,052 B2 | 4/2004 | Mills |
| 6,733,511 B2 | 5/2004 | Hall et al. |
| 6,740,103 B2 | 5/2004 | Hall et al. |
| 6,752,800 B1 | 6/2004 | Winston et al. |

(56) References Cited

U.S. PATENT DOCUMENTS

| | | |
|---|---|---|
| 6,755,816 B2 | 6/2004 | Ritter et al. |
| 6,811,544 B2 | 11/2004 | Schaer |
| 6,814,733 B2 | 11/2004 | Schwartz et al. |
| 6,820,614 B2 | 11/2004 | Bonutti |
| 6,834,201 B2 | 12/2004 | Gillies et al. |
| 6,842,639 B1 | 1/2005 | Winston et al. |
| 6,852,109 B2 | 2/2005 | Winston et al. |
| 6,855,143 B2 | 2/2005 | Davison et al. |
| 6,860,856 B2 | 3/2005 | Ward et al. |
| 6,869,431 B2 | 3/2005 | Maguire et al. |
| 6,911,026 B1 | 6/2005 | Hall et al. |
| 6,951,554 B2 | 10/2005 | Johansen et al. |
| 6,951,555 B1 | 10/2005 | Suresh et al. |
| 6,955,675 B2 | 10/2005 | Jain |
| 6,970,732 B2 | 11/2005 | Winston et al. |
| 6,980,843 B2 | 12/2005 | Eng et al. |
| 7,029,470 B2 | 4/2006 | Francischelli et al. |
| 7,056,294 B2 | 6/2006 | Khairkhahan et al. |
| 7,083,566 B2 | 8/2006 | Tornes et al. |
| 7,112,197 B2 | 9/2006 | Hartley et al. |
| 7,335,197 B2 | 2/2008 | Sage et al. |
| 7,618,430 B2 | 11/2009 | Scheib |
| 7,651,492 B2 | 1/2010 | Wham |
| 7,666,203 B2 | 2/2010 | Chanduszko et al. |
| 7,678,081 B2 | 3/2010 | Whiting et al. |
| 7,678,118 B2 | 3/2010 | Bates et al. |
| 7,682,360 B2 | 3/2010 | Guerra |
| 7,828,796 B2 | 11/2010 | Wong et al. |
| 7,900,928 B2 | 3/2011 | Held et al. |
| 8,192,425 B2 | 6/2012 | Mirza et al. |
| 8,246,617 B2 | 8/2012 | Welt et al. |
| 8,257,323 B2 | 9/2012 | Joseph et al. |
| 8,388,549 B2 | 3/2013 | Paul et al. |
| 8,500,697 B2 | 8/2013 | Kurth et al. |
| 9,445,895 B2 | 9/2016 | Kreidler |
| 9,656,046 B2 | 5/2017 | Liungman |
| 10,111,623 B2 | 10/2018 | Jung et al. |
| 11,339,579 B1 | 5/2022 | Stearns |
| 11,369,405 B2* | 6/2022 | Vardi ............... A61B 17/3478 |
| 11,497,552 B2* | 11/2022 | Morales ............. A61N 1/36067 |
| 2001/0012934 A1 | 8/2001 | Chandrasekaran et al. |
| 2001/0021867 A1 | 9/2001 | Kordis et al. |
| 2002/0019644 A1 | 2/2002 | Hastings et al. |
| 2002/0022781 A1 | 2/2002 | McIntire et al. |
| 2002/0022836 A1 | 2/2002 | Goble et al. |
| 2002/0035361 A1 | 3/2002 | Houser et al. |
| 2002/0087153 A1 | 7/2002 | Roschak et al. |
| 2002/0087156 A1 | 7/2002 | Maguire et al. |
| 2002/0111618 A1 | 8/2002 | Stewart et al. |
| 2002/0123749 A1 | 9/2002 | Jain |
| 2002/0147485 A1 | 10/2002 | Mamo et al. |
| 2002/0169377 A1 | 11/2002 | Khairkhahan et al. |
| 2002/0188302 A1 | 12/2002 | Berg et al. |
| 2002/0198521 A1 | 12/2002 | Maguire |
| 2003/0032929 A1 | 2/2003 | McGuckin |
| 2003/0040742 A1 | 2/2003 | Underwood et al. |
| 2003/0144658 A1 | 7/2003 | Schwartz et al. |
| 2003/0158480 A1 | 8/2003 | Tornes et al. |
| 2003/0163153 A1 | 8/2003 | Scheib |
| 2003/0225392 A1 | 12/2003 | McMichael et al. |
| 2004/0015162 A1 | 1/2004 | McGaffigan |
| 2004/0024396 A1 | 2/2004 | Eggers |
| 2004/0030328 A1 | 2/2004 | Eggers et al. |
| 2004/0044350 A1 | 3/2004 | Martin et al. |
| 2004/0073243 A1 | 4/2004 | Sepetka et al. |
| 2004/0077948 A1 | 4/2004 | Violante et al. |
| 2004/0116851 A1 | 6/2004 | Johansen et al. |
| 2004/0127963 A1 | 7/2004 | Uchida et al. |
| 2004/0133113 A1 | 7/2004 | Krishnan |
| 2004/0133130 A1 | 7/2004 | Ferry et al. |
| 2004/0143256 A1 | 7/2004 | Bednarek |
| 2004/0147950 A1 | 7/2004 | Mueller et al. |
| 2004/0181213 A1 | 9/2004 | Gondo |
| 2004/0230188 A1 | 11/2004 | Cioanta et al. |
| 2005/0004585 A1 | 1/2005 | Hall et al. |
| 2005/0010208 A1 | 1/2005 | Winston et al. |
| 2005/0049628 A1 | 3/2005 | Schweikert et al. |
| 2005/0059966 A1 | 3/2005 | McClurken et al. |
| 2005/0065507 A1 | 3/2005 | Hartley et al. |
| 2005/0085806 A1 | 4/2005 | Auge et al. |
| 2005/0096529 A1 | 5/2005 | Cooper et al. |
| 2005/0101984 A1 | 5/2005 | Chanduszko et al. |
| 2005/0119556 A1 | 6/2005 | Gillies et al. |
| 2005/0137527 A1 | 6/2005 | Kunin |
| 2005/0149012 A1 | 7/2005 | Penny et al. |
| 2005/0203504 A1 | 9/2005 | Wham et al. |
| 2005/0203507 A1 | 9/2005 | Truckai et al. |
| 2005/0261607 A1 | 11/2005 | Johansen et al. |
| 2005/0288631 A1 | 12/2005 | Lewis et al. |
| 2006/0041253 A1 | 2/2006 | Newton et al. |
| 2006/0074398 A1 | 4/2006 | Whiting et al. |
| 2006/0079769 A1 | 4/2006 | Whiting et al. |
| 2006/0079787 A1 | 4/2006 | Whiting et al. |
| 2006/0079884 A1 | 4/2006 | Manzo et al. |
| 2006/0085054 A1 | 4/2006 | Zikorus et al. |
| 2006/0089638 A1 | 4/2006 | Carmel et al. |
| 2006/0106375 A1 | 5/2006 | Werneth et al. |
| 2006/0135962 A1 | 6/2006 | Kick et al. |
| 2006/0142756 A1 | 6/2006 | Davies et al. |
| 2006/0189972 A1 | 8/2006 | Grossman |
| 2006/0241586 A1 | 10/2006 | Wilk |
| 2006/0247672 A1 | 11/2006 | Vidlund et al. |
| 2006/0264927 A1 | 11/2006 | Ryan |
| 2006/0276710 A1 | 12/2006 | Krishnan |
| 2007/0060879 A1 | 3/2007 | Weitzner et al. |
| 2007/0066975 A1 | 3/2007 | Wong et al. |
| 2007/0118099 A1 | 5/2007 | Trout, III |
| 2007/0123964 A1 | 5/2007 | Davies et al. |
| 2007/0167775 A1 | 7/2007 | Kochavi et al. |
| 2007/0173939 A1 | 7/2007 | Kim et al. |
| 2007/0208256 A1 | 9/2007 | Marilla |
| 2007/0225681 A1 | 9/2007 | House |
| 2007/0270791 A1 | 11/2007 | Wang et al. |
| 2008/0039865 A1 | 2/2008 | Shaher et al. |
| 2008/0042360 A1 | 2/2008 | Veikley |
| 2008/0086120 A1 | 4/2008 | Mirza et al. |
| 2008/0097213 A1 | 4/2008 | Carlson et al. |
| 2008/0108987 A1 | 5/2008 | Bruszewski et al. |
| 2008/0146918 A1 | 6/2008 | Magnin et al. |
| 2008/0171934 A1 | 7/2008 | Greenan et al. |
| 2008/0208121 A1 | 8/2008 | Youssef et al. |
| 2008/0275439 A1 | 11/2008 | Francischelli et al. |
| 2009/0105742 A1 | 4/2009 | Kurth et al. |
| 2009/0138009 A1 | 5/2009 | Viswanathan et al. |
| 2009/0163850 A1 | 6/2009 | Betts et al. |
| 2009/0177114 A1 | 7/2009 | Chin et al. |
| 2009/0264977 A1 | 10/2009 | Bruszewski et al. |
| 2010/0087789 A1 | 4/2010 | Leeflang et al. |
| 2010/0125282 A1 | 5/2010 | Machek et al. |
| 2010/0168684 A1 | 7/2010 | Ryan |
| 2010/0179632 A1 | 7/2010 | Bruszewski et al. |
| 2010/0191142 A1 | 7/2010 | Paul et al. |
| 2010/0194047 A1 | 8/2010 | Sauerwine |
| 2011/0046619 A1 | 2/2011 | Ducharme |
| 2011/0152716 A1 | 6/2011 | Chudzik et al. |
| 2011/0160592 A1 | 6/2011 | Mitchell |
| 2011/0190763 A1 | 8/2011 | Urban et al. |
| 2012/0232546 A1 | 9/2012 | Mirza et al. |
| 2012/0265055 A1 | 10/2012 | Melsheimer et al. |
| 2012/0330156 A1 | 12/2012 | Brown et al. |
| 2013/0184551 A1 | 7/2013 | Paganelli et al. |
| 2013/0184735 A1 | 7/2013 | Fischell et al. |
| 2013/0282084 A1 | 10/2013 | Mathur et al. |
| 2014/0206987 A1 | 7/2014 | Urbanski et al. |
| 2014/0243822 A1 | 8/2014 | Farin et al. |
| 2014/0296769 A1 | 10/2014 | Hyde et al. |
| 2015/0032103 A1* | 1/2015 | McLawhorn ...... A61B 18/1492 606/41 |
| 2015/0066010 A1* | 3/2015 | McLawhorn ...... A61B 18/1492 606/34 |
| 2016/0166314 A1 | 6/2016 | Hancock et al. |
| 2016/0220741 A1 | 8/2016 | Garrison et al. |
| 2017/0231647 A1 | 8/2017 | Saunders et al. |
| 2018/0055496 A1 | 3/2018 | Hou et al. |

(56) References Cited

U.S. PATENT DOCUMENTS

| | | |
|---|---|---|
| 2019/0021763 A1 | 1/2019 | Zhou et al. |
| 2019/0142406 A1 | 5/2019 | Amplatz et al. |
| 2019/0247035 A1 | 8/2019 | Gittard et al. |
| 2019/0298411 A1* | 10/2019 | Davies .................. A61B 90/39 |
| 2020/0289196 A1* | 9/2020 | Arevalos ........ A61B 17/320016 |
| 2020/0345487 A1 | 11/2020 | Christianson et al. |

* cited by examiner

SECTION A-A

ELONGATED MEDICAL SHEATH

TECHNICAL FIELD

This document relates to the technical field of (and is not limited to) an elongated medical sheath (and method therefor).

BACKGROUND

Known medical devices are configured to facilitate a medical procedure, and help healthcare providers diagnose and/or treat medical conditions of sick patients.

SUMMARY

It will be appreciated that there exists a need to mitigate (at least in part) at least one problem associated with existing (known) elongated medical sheaths. After much study of, and experimentation with, the existing (known) elongated medical sheaths, an understanding (at least in part) of the problem and its solution have been identified (at least in part) and are articulated (at least in part) as follows:

There is a need to access and deliver medical devices, such as cardiac devices from the right atrium to the left atrium of the heart of a patient. Cryoablation, mitral valve replacement and/or left atrial appendage closure are examples of procedures that require the use of larger sheaths. Therefore, tissue dilation may be necessary to allow for transcatheter delivery of these medical devices to the left atrium of the heart. Known medical methods to dilate the initial puncture include the use of several dilators or the use of a balloon.

It may be desirable to deploy relatively smaller form-factor medical sheaths; unfortunately, known medical sheaths having a relatively smaller form factor are not available for medical procedures which require the larger form-factor medical sheaths.

To mitigate, at least in part, at least one problem associated with the existing technology, there is provided (in accordance with a major aspect) an apparatus. The apparatus includes and is not limited to (comprises) an elongated medical sheath configured to be movable and positionable proximate to a biological feature of a patient. An expandable-and-collapsible support structure is configured to be selectively movable, at least in part, between an interior of the elongated medical sheath and an exterior of the elongated medical sheath. An energy-emitting assembly is supported by the expandable-and-collapsible support structure.

To mitigate, at least in part, at least one problem associated with the existing technology, there is provided (in accordance with a major aspect) a method for operating an elongated medical sheath configured to be movable and positionable proximate to a biological feature of a patient. The method includes and is not limited to (comprises) selectively moving, at least in part, an expandable-and-collapsible support structure supporting an energy-emitting assembly between an interior of the elongated medical sheath and an exterior of the elongated medical sheath.

Other aspects and features of the non-limiting embodiments may become apparent to those skilled in the art upon review of the following detailed description of the non-limiting embodiments with the accompanying drawings. This Summary is provided to introduce concepts in simplified form that are further described below in the Detailed Description. This Summary is not intended to identify potentially key features or possible essential features of the disclosed subject matter, and is not intended to describe each disclosed embodiment or every implementation of the disclosed subject matter. Many other novel advantages, features, and relationships will become apparent as this description proceeds. The figures and the description that follow more particularly exemplify illustrative embodiments.

BRIEF DESCRIPTION OF THE DRAWINGS

The non-limiting embodiments may be more fully appreciated by reference to the following detailed description of the non-limiting embodiments when taken in conjunction with the accompanying drawings, in which.

Figure 1A:
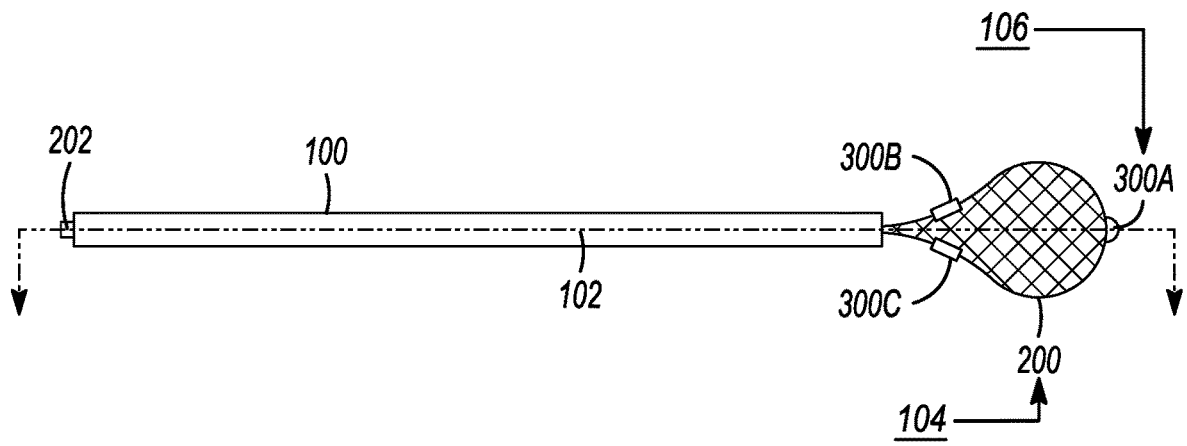
FIG. 1A, FIG. 1B and FIG. 2 depict a side view (FIG. 1A), an end view (FIG. 1B) and a cross-sectional view (FIG. 2) of embodiments (implementations) of an elongated medical sheath.

The drawings are not necessarily to scale and may be illustrated by phantom lines, diagrammatic representations and fragmentary views. In certain instances, details unnecessary for an understanding of the embodiments (and/or details that render other details difficult to perceive) may have been omitted. Corresponding reference characters indicate corresponding components throughout the several figures of the drawings. Elements in the several figures are illustrated for simplicity and clarity and have not been drawn to scale. The dimensions of some of the elements in the figures may be emphasized relative to other elements for facilitating an understanding of the various disclosed embodiments. In addition, common, and well-understood, elements that are useful in commercially feasible embodiments are often not depicted to provide a less obstructed view of the embodiments of the present disclosure.

LISTING OF REFERENCE NUMERALS USED IN THE DRAWINGS medical sheath 100
elongated lumen 102
expandable-and-collapsible support structure 104
energy-emitting assembly 106
expandable-and-collapsible cage structure 200
elongated member 202
energy-emitting devices (300A, 300B, 300C)
generator 500
cable 502
biological feature 900
patient 902

DETAILED DESCRIPTION OF THE NON-LIMITING EMBODIMENT(S)

The following detailed description is merely exemplary and is not intended to limit the described embodiments or the application and uses of the described embodiments. As used, the word "exemplary" or "illustrative" means "serving as an example, instance, or illustration." Any implementation described as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure. The scope of the disclosure is defined by the claims. For the description, the terms "upper," "lower," "left," "rear," "right," "front," "vertical," "horizontal," and derivatives thereof shall relate to the examples as oriented in the drawings. There is no intention to be bound by any expressed or implied theory in the preceding Technical Field, Background, Summary or the following detailed description. It is also to be understood that the devices and processes illustrated in the attached drawings, and described in the following specification, are exemplary embodiments (examples), aspects and/or concepts defined in the appended claims. Hence, dimensions and other physical characteristics relating to the embodiments disclosed are not to be considered as limiting, unless the claims expressly state otherwise. It is understood that the phrase "at least one" is equivalent to "a". The aspects (examples, alterations, modifications, options, variations, embodiments and any equivalent thereof) are described regarding the drawings. It should be understood that the disclosure is limited to the subject matter provided by the claims, and that the disclosure is not limited to the particular aspects depicted and described. It will be appreciated that the scope of the meaning of a device configured to be coupled to an item (that is, to be connected to, to interact with the item, etc.) is to be interpreted as the device being configured to be coupled to the item, either directly or indirectly. Therefore, "configured to" may include the meaning "either directly or indirectly" unless specifically stated otherwise.

Figure 1B:
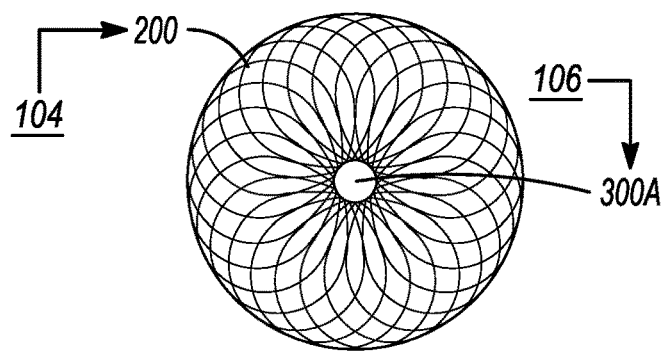
Figure 2:
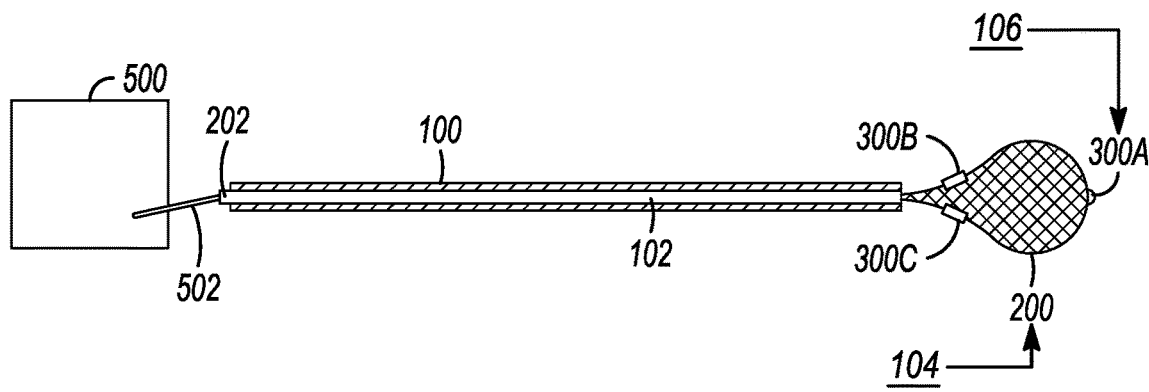

FIG. 1A, FIG. 1B and FIG. 2 depict a side view (FIG. 1A), and end view (FIG. 1B) and a cross-sectional view (FIG. 2) of embodiments (implementations) of an elongated medical sheath 100.

Figure 3:
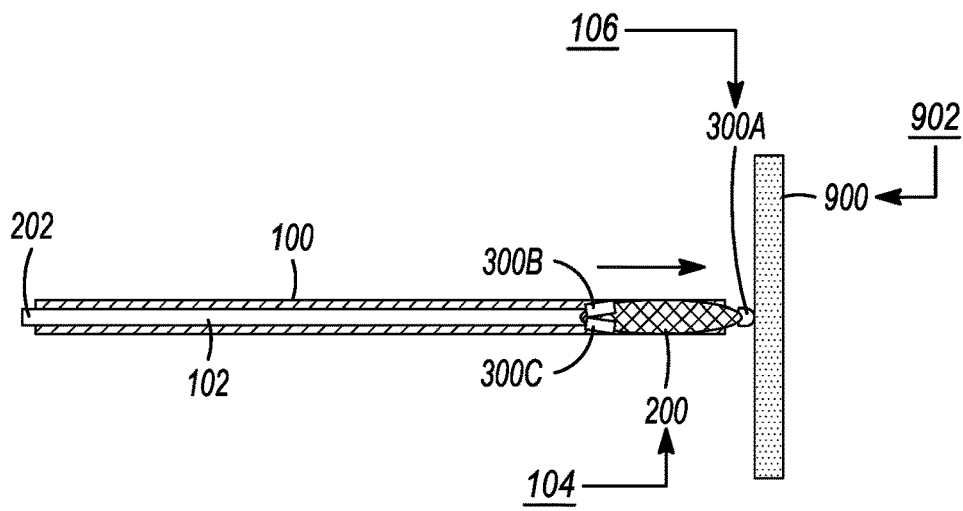
FIG. 3, FIG. 4 and FIG. 5 depict cross-sectional views of embodiments (implementations) of the elongated medical sheath of FIG. 1A.
Figure 4:
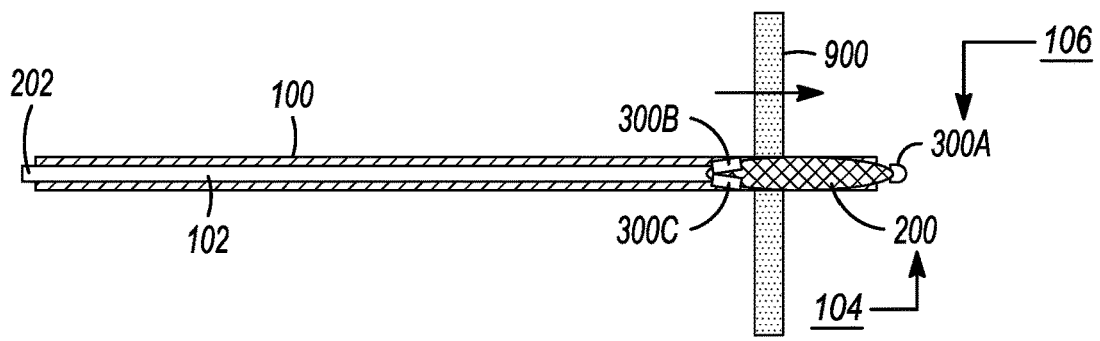
Figure 5:
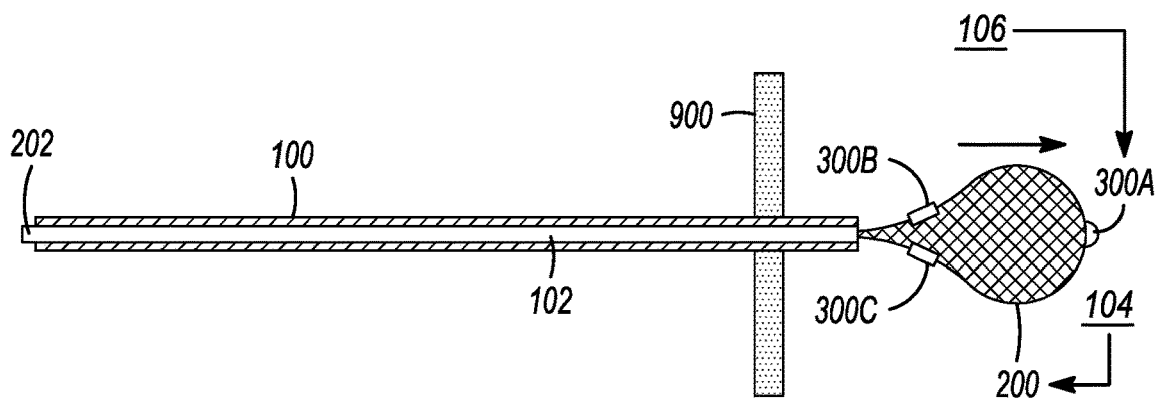

Referring to the embodiments (implementations) as depicted in FIG. 1A and FIG. 1B, an elongated medical sheath 100 is configured to be movable (and positionable) proximate to a biological feature 900 (such as a biological wall) of a patient 902. An embodiment of the biological feature 900 of the patient 902 is depicted in FIG. 3. The elongated medical sheath 100 is configured (preferably) to be inserted into a confined space defined by a living body (the patient). An expandable-and-collapsible support structure 104 is configured to be selectively movable, at least in part, between an interior of the elongated medical sheath 100 (as depicted in FIG. 3) and an exterior of the elongated medical sheath 100 (as depicted in FIG. 5); this technical feature is depicted in the embodiments of FIG. 3, FIG. 4 and FIG. 5. It will be appreciated that, as depicted in FIG. 1A, the expandable-and-collapsible support structure 104 is selectively moved, at least in part, from the interior of the elongated medical sheath 100, and is positioned, at least in part, at the exterior of the elongated medical sheath 100. An energy-emitting assembly 106 is supported by (is configured to be supported by) the expandable-and-collapsible support structure 104. The elongated medical sheath 100 is (preferably) configured to receive and guide the expandable-and-collapsible support structure 104 into the confined space defined by the patient. The elongated medical sheath 100 includes, preferably, a flexible tube (and any equivalent thereof). The elongated medical sheath 100 forms (defines) an elongated lumen 102 extending between the distal section and the proximal section of the elongated medical sheath 100. The elongated lumen 10 is configured to slidably receive the energy-emitting assembly 106; this is done in such a way that the energy-emitting assembly 106 may be movable along the interior of the elongated medical sheath 100.

Referring to the embodiments (implementations) as depicted in FIG. 1A and FIG. 1B, the elongated medical sheath 100 may provide, for instance, an alternative to balloon atrial septostomy while not requiring, advantageously, the exchange of multiple conventional medical dilators (if so desired).

Referring to the embodiments (implementations) as depicted in FIG. 1A and FIG. 1B, the elongated medical sheath 100 includes biocompatible material properties suitable for performance (such as, electric dielectric strength, thermal insulation, electrical insulation, corrosion, water resistance, heat resistance, etc.) for compliance with industrial and regulatory safety standards (or compatible for medical usage), etc. Reference is made to the following publication for consideration in the selection of a suitable material: Plastics in Medical Devices: Properties, Requirements, and Applications; 2nd Edition; author: Vinny R. Sastri; hardcover ISBN: 9781455732012; published: 21 Nov. 2013; publisher: Amsterdam [Pays-Bas]: Elsevier/William Andrew, [2014].

Referring to the embodiments (implementations) as depicted in FIG. 1A and FIG. 1B, the expandable-and-collapsible support structure 104 includes (preferably) a shape-memory material configured to be manipulated and/or deformed followed by a return to the original shape that the shape-memory material was set in (prior to manipulation). Shape-memory materials (SMMs) are known and not further described in detail. Shape-memory materials are configured to recover their original shape from a significant and seemingly plastic deformation in response to a particular stimulus applied to the shape-memory material. This is known as the shape memory effect (SME). Superelasticity (in alloys) may be observed once the shape-memory material is deformed under the presence (an application) of a stimulus force.

Referring to the embodiments (implementations) as depicted in FIG. 1A and FIG. 1B, the energy-emitting assembly 106 includes (preferably) energy-emitting devices (300A, 300B, 300C). The energy-emitting devices (300A, 300B, 300C) are supported by the expandable-and-collapsible support structure 104. The energy-emitting devices (300A, 300B, 300C) are configured to selectively emit energy (such as radiofrequency energy). The energy-emitting devices (300A, 300B, 300C) are configured to be connected (electrically connected) to an energy source 500 (depicted in FIG. 2). The energy-emitting devices (300A, 300B, 300C) include (preferably) electrodes supported by the expandable-and-collapsible support structure 104. The electrodes are configured to selectively emit energy (such as radiofrequency energy) in a manner that is, preferably, similar to the BAYLIS (TRADEMARK) POWERWIRE (REGISTERED TRADEMARK) radiofrequency guidewire manufactured by BAYLIS MEDICAL COMPANY (headquartered in Canada).

Referring to the embodiments (implementations) as depicted in FIG. 1A and FIG. 1B, the energy-emitting assembly 106 is (preferably) configured to be detectable by an electroanatomical mapping system (known and not depicted), which may include fluoroscopy mapping systems (if so desired, but may not be preferred for some embodiments). The electroanatomical mapping system may include a nonfluoroscopy mapping system, such as, and not limited to, (A) the CARTO EP (TRADEMARK) mapping system (manufactured by BIOSENSE WEBSTER based in the USA), (B) the ENSITE PRECISION (TRADEMARK) cardiac mapping system (manufactured by Abbott Laboratories based in the USA), (C) the LOCALISA (TRADEMARK) intracardiac mapping system (manufactured by MEDTRONICS INC., based in the USA), and (D) the RHYTHMIA HDx (TRADEMARK) mapping system (manufactured by Boston Scientific Corp., based in the USA).

Referring to the embodiment (implementation) as depicted in FIG. 1A, FIG. 1B and FIG. 2, the expandable-and-collapsible support structure 104 includes (preferably) an expandable-and-collapsible cage structure 200 (such as a flexible wire cage and any equivalent thereof). The expandable-and-collapsible cage structure 200 is configured to be selectively movable, at least in part, between the interior of the elongated medical sheath 100 (as depicted in FIG. 3) and the exterior of the elongated medical sheath 100 (as depicted in FIG. 5). Returning back to FIG. 2, if desired, an elongated member 202 extends from the expandable-and-collapsible cage structure. The elongated member 202 is configured to be movable along the interior of the elongated medical sheath 100. The distal section of the elongated member 202 is attached to the expandable-and-collapsible cage structure 200. The elongated member 202 is configured to selectively move the expandable-and-collapsible cage structure 200 relative to the interior of the elongated medical sheath 100, etc. A proximal section of the elongated member 202 extends from the proximal end of the elongated medical sheath 100 (for user-control purposes).

Figure 6:
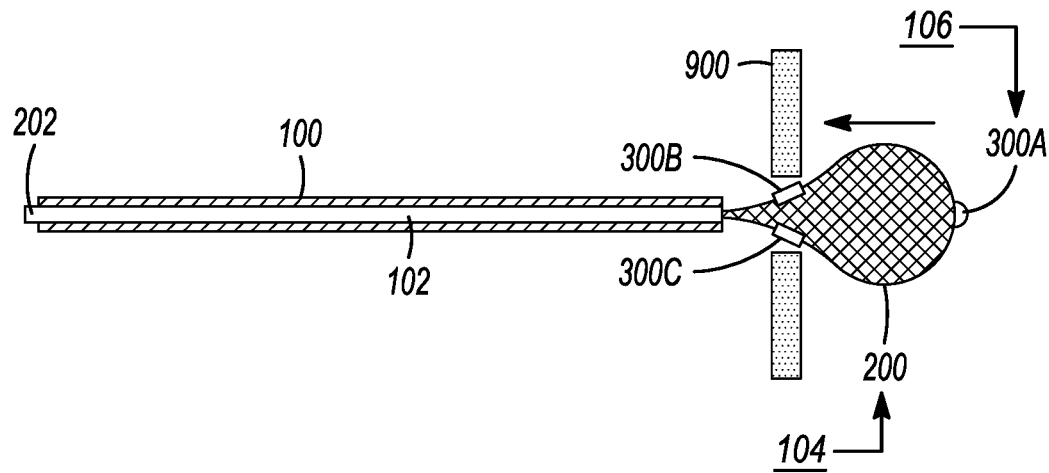
FIG. 6 and FIG. 7 depict cross-sectional views of embodiments (implementations) of the elongated medical sheath of FIG. 1A.

Referring to the embodiments (implementations) as depicted in FIG. 1A, FIG. 3, FIG. 4 and FIG. 6, the expandable-and-collapsible cage structure 200 has (supports) the energy-emitting devices (300A, 300B, 300C), as depicted in FIG. 1A. The expandable-and-collapsible cage structure 200 has a distal section and a proximal section, as depicted in FIG. 1A. At least one, or more, of the energy-emitting devices (300A, 300B, 300C), such as the energy-emitting device 300A, is/are positioned at the distal section of the expandable-and-collapsible cage structure 200, and is/are configured to puncture the biological feature 900 (such as the septum of the heart), as depicted in FIG. 3 (in response to forward movement of the expandable-and-collapsible cage structure 200 toward the biological feature 900, as depicted in FIG. 3 and FIG. 4). At least one (or more) of the energy-emitting devices (300A, 300B, 300C), such as the energy-emitting devices (300B, 300C) is/are positioned at the proximal section of the expandable-and-collapsible cage structure 200, and is/are configured to dilate the puncture hole and create (form) a larger hole (such as septal hole) by dilation of the initially formed puncture hole, as depicted in FIG. 6 (in response to rearward movement of the expandable-and-collapsible cage structure 200 toward the biological feature 900, after formation of the puncture hole).

Referring to the embodiments (implementations) as depicted in FIG. 1A, FIG. 3, FIG. 4 and FIG. 6, the expandable-and-collapsible cage structure 200 may be used to create or form larger holes in the biological feature (a wall, the interatrial septum, etc.) as described above, and/or may be used for tissue dilation in biological features or structures including, for instance, the interventricular septum and blood vessels, etc.

Referring to the embodiments (implementations) as depicted in FIG. 1A, FIG. 1B and FIG. 3, the expandable-and-collapsible cage structure 200 (also called a selectively flexible wire cage) is depicted. For instance, the wires that form the expandable-and-collapsible cage structure 200 may be made from a stiffer material with shape memory capability, for example, nitinol may allow the expandable-and-collapsible cage structure 200 to form the desired shape after exiting from the distal section of the elongated medical sheath 100. The wires may be arranged in a cross-hatch pattern, if so desired, for improved functionality, etc. The expandable-and-collapsible cage structure 200 is configured to fit in, and be movable along, the interior (such as the elongated lumen 102) of the elongated medical sheath 100. Once the expandable-and-collapsible cage structure 200 is received in the interior of the elongated medical sheath 100, the expandable-and-collapsible cage structure 200 is placed in a storage condition (undeployed state, as depicted in FIG. 3). The expandable-and-collapsible cage structure 200, once deployed (as depicted in FIG. 1A), forms a tear drop shape in an expanded state (deployed condition). The expandable-and-collapsible cage structure 200, once deployed, forms (preferably) a tapered proximal section (a tear drop shape) in an expanded state (deployed condition). The expandable-and-collapsible cage structure 200, once deployed, is configured to expand radially and at the distal section of the expandable-and-collapsible cage structure 200. The elbows and/or bends of the expandable-and-collapsible cage structure 200 may be made of a relatively softer metal.

Referring to the embodiments (implementations) as depicted in FIG. 1A and FIG. 1B, at least one of the energy-emitting devices (300A, 300B, 300C) may be positioned at the distal section and at the proximal section of the expandable-and-collapsible cage structure 200. The energy-emitting devices (300A, 300B, 300C) may be rounded so that they are (preferably) atraumatic. The energy-emitting devices (300A, 300B, 300C) are configured to selectively emit energy (such as radiofrequency energy) for vaporizing tissue (such as the biological feature 900 of FIG. 3). The equivalent devices of the energy-emitting devices (300A, 300B, 300C) may include mechanical sharp cutting edges configured to cut through tissue in response to the application of a mechanical force. The distal instances of the energy-emitting devices (300A, 300B, 300C) may be replaced with at least one or more sharp tips, and the proximal instances of the energy-emitting devices (300A, 300B, 300C) may be replaced with cutting blades, etc. It will be appreciated that unsafe sharp tips and/or cutting blades might cause inadvertent damage to cardiac structures, and that mechanical cutting tips and/or blades might be more appropriate for other parts of the anatomy of the patient, etc. Therefore, it will be appreciated that the energy-emitting assembly 106 may be substituted (at least in part) with a mechanical tissue-cutting assembly (such as a blade, a cutting tip, and any equivalent thereof, etc.) supported by the expandable-and-collapsible support structure 104.

Referring to the embodiment (implementation) as depicted in FIG. 2, the elongated medical sheath 100 includes an elongated shaft made of an electrically-insulated material. There may be insulated wires that connect to the energy-emitting devices (300A, 300B, 300C), run the length (within the interior) of the elongated medical sheath 100, and then connect to a generator 500 via a cable 502. The generator 500 is, preferably, configured to generate energy (such as radiofrequency energy, and any equivalent thereof). The generator 500 is, preferably, configured to select and control the emission of energy from a desired instance of the energy-emitting devices (300A, 300B, 300C), in order to emit energy as needed (when needed) by at least one of the energy-emitting devices (300A, 300B, 300C), as well as (preferably) for a time duration and/or with a shaped energy waveform, etc.

FIG. 3, FIG. 4 and FIG. 5 depict cross-sectional views of embodiments (implementations) of the elongated medical sheath 100 of FIG. 1A.

Referring to the embodiments (implementations) as depicted in FIG. 3 and FIG. 5, there is depicted a method. The method, generally, is for operating the elongated medical sheath 100. The method includes selectively moving, at least in part, the expandable-and-collapsible support structure 104 supporting the energy-emitting assembly 106 between the interior of the elongated medical sheath 100 (as depicted in FIG. 3) and the exterior of the elongated medical sheath 100 (as depicted in FIG. 5).

Referring to the embodiment (implementation) as depicted in FIG. 3, in the first state (storage state or collapsed state), the expandable-and-collapsible cage structure 200 is in an undeployed form in a low-profile form factor (that is, fitted to be received in the interior of the elongated medical sheath 100). The distal end section of the expandable-and-collapsible cage structure 200 has at least one of the energy-emitting devices (300A, 300B, 300C). Energy (such as radiofrequency energy) may be selectively emitted from at least one energy-emitting device 300A (or from the energy-emitting assembly 106 in general terms) toward the biological feature 900 (such as the septum) for the purposes of puncturing the biological feature 900. After formation of the puncture hole, the energy-emitting device 300A is selectively deactivated, and the expandable-and-collapsible cage structure 200 may be moved forwardly through the puncture hole (while the expandable-and-collapsible cage structure 200 remains in the undeployed state).

Referring to the embodiment (implementation) as depicted in FIG. 4, after formation of the puncture hole, the energy-emitting device 300A is deactivated, and the distal section of the expandable-and-collapsible support structure 104 (or the expandable-and-collapsible cage structure 200) may be moved to cross (pass through) the biological feature 900 via the puncture hole formed through the biological feature 900; that is, the expandable-and-collapsible cage structure 200 is moved to cross through the puncture hole formed through the biological feature 900. This action is done in response to forward movement of the elongated medical sheath 100. This movement is done, preferably, while the expandable-and-collapsible cage structure 200 remains within the interior of the elongated medical sheath 100.

Referring to the embodiment (implementation) as depicted in FIG. 5, after the puncture hole is formed through the biological wall 900, the energy-emitting device 300A is deactivated. Once the energy-emitting device 300A is deactivated, the expandable-and-collapsible cage structure 200 may be further advanced from the interior of the elongated medical sheath 100, past the puncture hole, and extended (at least in part) past the biological feature 900; in this manner, the expandable-and-collapsible cage structure 200 is deployed from the interior of the elongated medical sheath 100 to the exterior of the elongated medical sheath 100. For instance, the expandable-and-collapsible cage structure 200 may be deployed (such as, into the left atrium of the heart) to the second state (also called the deployment state). In the deployment state, the expandable-and-collapsible cage structure 200 is configured to expand (is expanded and/or expands) into a biased shape as depicted. For instance, once deployed, the expandable-and-collapsible cage structure 200 may have a larger radius in a middle section in comparison to the radius of a distal end section of the expandable-and-collapsible cage structure 200.

Figure 7:
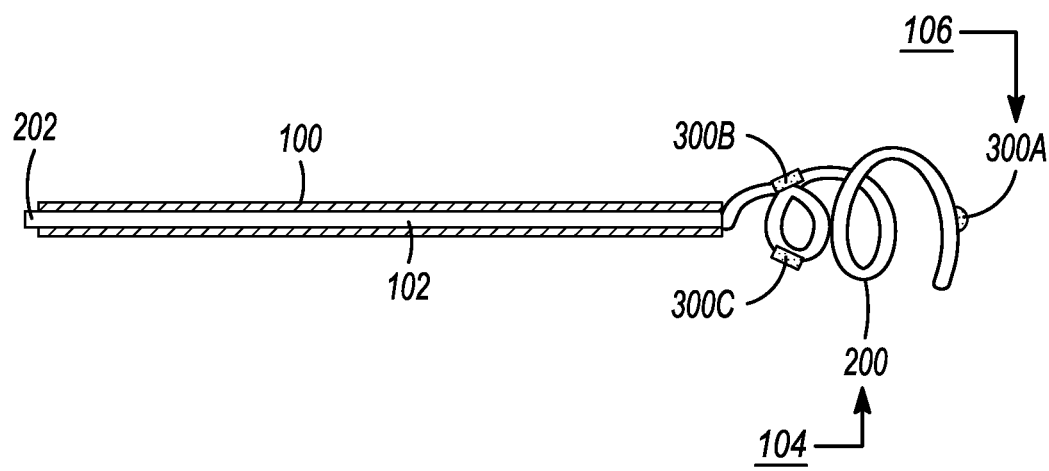

FIG. 6 and FIG. 7 depict cross-sectional views of embodiments (implementations) of the elongated medical sheath 100 of FIG. 1A.

Referring to the embodiment (implementation) as depicted in FIG. 6, the proximal section of the expandable-and-collapsible cage structure 200 has (preferably) at least one or more instances of the energy-emitting devices (300B, 300C) configured to selectively emit energy (such as, radiofrequency energy) toward the puncture hole formed through the biological feature 900 while the elongated medical sheath 100 is retracted back into the interior of the elongated medical sheath 100 (such as, after the expandable-and-collapsible cage structure 200 is moved from the right atrium to the left atrium of the heart of the patient, etc.). Selective activation of at last one instance of the energy-emitting devices (300B, 300C), along with rearward movement of the expandable-and-collapsible cage structure 200 toward the initially formed puncture hole, dilates (at least in part) the initially formed puncture hole, thereby forming, advantageously, a larger puncture hole (such as a septal hole, etc.). Once the dilation of the puncture hole is completed, the energy-emitting devices (300B, 300C) are deactivated and the expandable-and-collapsible cage structure 200 may be fully retracted into the interior of the elongated medical sheath 100.

Referring to the embodiment (implementation) as depicted in FIG. 7, it will be appreciated that the expandable-and-collapsible cage structure 200 may form other shapes and/or arrangements in the deployed condition, such as a spiral-shaped formation (and any equivalent thereof), as depicted FIG. 7.

The following is offered as further description of the embodiments, in which any one or more of any technical feature (described in the detailed description, the summary and the claims) may be combinable with any other one or more of any technical feature (described in the detailed description, the summary and the claims). It is understood that each claim in the claims section is an open ended claim unless stated otherwise. Unless otherwise specified, relational terms used in these specifications should be construed to include certain tolerances that the person skilled in the art would recognize as providing equivalent functionality. By way of example, the term perpendicular is not necessarily limited to 90.0 degrees, and may include a variation thereof that the person skilled in the art would recognize as providing equivalent functionality for the purposes described for the relevant member or element. Terms such as "about" and "substantially", in the context of configuration, relate generally to disposition, location, or configuration that are either exact or sufficiently close to the location, disposition, or configuration of the relevant element to preserve operability of the element within the disclosure which does not materially modify the disclosure. Similarly, unless specifically made clear from its context, numerical values should be construed to include certain tolerances that the person skilled in the art would recognize as having negligible importance as they do not materially change the operability of the disclosure. It will be appreciated that the description and/or drawings identify and describe embodiments of the apparatus (either explicitly or inherently). The apparatus may include any suitable combination and/or permutation of the technical features as identified in the detailed description, as may be required and/or desired to suit a particular technical purpose and/or technical function. It will be appreciated that, where possible and suitable, any one or more of the technical features of the apparatus may be combined with any other one or more of the technical features of the apparatus (in any combination and/or permutation). It will be appreciated that persons skilled in the art would know that the technical features of each embodiment may be deployed (where possible) in other embodiments even if not expressly stated as such above. It will be appreciated that persons skilled in the art would know that other options may be possible for the configuration of the components of the apparatus to adjust to manufacturing requirements and still remain within the scope as described in at least one or more of the claims. This written description provides embodiments, including the best mode, and also enables the person skilled in the art to make and use the embodiments. The patentable scope may be defined by the claims. The written description and/or drawings may help to understand the scope of the claims. It is believed that all the crucial aspects of the disclosed subject matter have been provided in this document. It is understood, for this document, that the word "includes" is equivalent to the word "comprising" in that both words are used to signify an open-ended listing of assemblies, components, parts, etc. The term "comprising", which is synonymous with the terms "including," "containing," or "characterized by," is inclusive or open-ended and does not exclude additional, unrecited elements or method steps. Comprising (comprised of) is an "open" phrase and allows coverage of technologies that employ additional, unrecited elements. When used in a claim, the word "comprising" is the transitory verb (transitional term) that separates the preamble of the claim from the technical features of the disclosure. The foregoing has outlined the non-limiting embodiments (examples). The description is made for particular non-limiting embodiments (examples). It is understood that the non-limiting embodiments are merely illustrative as examples.

What is claimed is:

1. An apparatus, comprising:
   an elongated medical sheath configured to be movable and positionable proximate to a biological feature of a patient; and
   an expandable-and-collapsible support structure configured to be selectively movable, at least in part, between a collapsed state within an interior of the elongated medical sheath and an expanded state at an exterior of the elongated medical sheath, the expandable-and-collapsible support structure including an expandable-and-collapsible cage structure having a distal section and a proximal section; and
   an energy-emitting assembly being supported by the expandable-and-collapsible support structure, the energy-emitting assembly includes:
     energy-emitting devices, one or more of the energy-emitting devices being positioned at the distal section of the expandable-and-collapsible cage structure and being configured to puncture the biological feature of a patient while the expandable-and-collapsible cage structure is in a collapsed state.

2. The apparatus of claim 1, wherein:
   said energy-emitting devices include:
     electrodes being supported by the expandable-and-collapsible support structure.

3. The apparatus of claim 1, wherein:
   the expandable-and-collapsible support structure includes:
     an elongated member extending from the expandable-and-collapsible cage structure; and
     the elongated member is configured to be movable along the interior of the elongated medical sheath.

4. The apparatus of claim 3, wherein:
   at least one of the energy-emitting devices is positioned at the proximal section of the expandable-and-collapsible cage structure, and is configured to dilate a puncture hole.

5. The apparatus of claim 3, wherein:
   the expandable-and-collapsible cage structure is configured to fit in, and be movable along, the interior of the elongated medical sheath in such a way that once the expandable-and-collapsible cage structure is received in the interior of the elongated medical sheath, the expandable-and-collapsible cage structure is placed in a storage condition.

6. The apparatus of claim 3, wherein:
   the expandable-and-collapsible cage structure, once deployed, forms a tear drop shape in an expanded state.

7. The apparatus of claim 3, wherein:
   the expandable-and-collapsible cage structure, once deployed, forms a tapered proximal section in an expanded state.

8. The apparatus of claim 3, wherein:
   the expandable-and-collapsible cage structure, once deployed, is configured to expand radially at the distal section of the expandable-and-collapsible cage structure.

9. The apparatus of claim 3, wherein:
   the expandable-and-collapsible cage structure is configured to form a spiral-shaped formation.

10. The apparatus of claim 1, wherein elbows or bends of the expandable-and-collapsible support structure are formed of a metal softer than other portions of the expandable-and-collapsible support structure.

11. A method of operating an elongated medical sheath configured to be movable and positionable proximate to a biological feature of a patient, the method comprising:
    selectively moving, at least in part, an expandable-and-collapsible support structure supporting an energy-emitting assembly between a collapsed state within an interior of the elongated medical sheath and an expanded state at an exterior of the elongated medical sheath, wherein the expandable-and-collapsible support structure includes an expandable-and-collapsible cage structure having a distal section and a proximal section, and the energy-emitting assembly includes energy-emitting devices, one or more of the energy-emitting devices being positioned at and supported by the distal section of the expandable-and-collapsible cage structure and being configured to puncture the biological feature of a patient while the expandable-and-collapsible cage is in a collapsed state.

12. The method of claim 11, further comprising:
    using the one or more of the energy-emitting devices positioned at the distal section of the expandable-and-collapsible cage structure for formation of a puncture hole through a biological wall.

13. The method of claim 11, further comprising:
    using at least one of the energy-emitting devices of the energy-emitting assembly for dilating a puncture hole formed through a biological wall.

14. The method of claim 11, further comprising:
    using the one or more of the energy-emitting devices positioned at the distal section of the expandable-and-collapsible cage structure for selective emission of energy to form a puncture hole through the biological wall.

15. The method of claim 14, further comprising:
using at least one of the energy-emitting devices of the energy-emitting assembly for selective emission of energy to dilate a puncture hole formed through a biological wall.

16. An apparatus, comprising:
an elongated medical sheath configured to be movable and positionable proximate to a biological feature of a patient; and
an expandable-and-collapsible cage configured to be selectively movable between a collapsed state within an interior of the elongated medical sheath and an expanded state at an exterior of the elongated medical sheath, the expandable-and collapsible cage having a distal section and a proximal section;
an elongated member extending from the expandable-and-collapsible cage; and
electrodes supported by the expandable-and-collapsible cage, at least one of the electrodes being positioned at the distal section of the expandable-and-collapsible cage and being configured to puncture the biological feature of a patient while the expandable-and-collapsible cage structure is in a collapsed state.

17. The apparatus of claim 16, wherein at least one of the electrodes is positioned at the proximal section of the expandable-and-collapsible cage, and is configured to dilate the puncture.

18. The apparatus of claim 16, wherein the expandable-and-collapsible cage forms a tear drop shape in an expanded state.

19. The apparatus of claim 16, wherein the expandable-and-collapsible cage forms a tapered proximal section in an expanded state.

20. The apparatus of claim 16, wherein elbows or bends of the expandable-and-collapsible cage are formed of a metal softer than other portions of the expandable-and-collapsible cage.

* * * * *